US010428828B2

(12) United States Patent
Canatella et al.

(10) Patent No.: US 10,428,828 B2
(45) Date of Patent: Oct. 1, 2019

(54) CENTRIFUGAL PUMPS FOR MEDICAL USES

(71) Applicant: Terumo Cardiovascular Systems Corporation, Ann Arbor, MI (US)

(72) Inventors: Timothy John Canatella, Jarrettsville, MD (US); Gregory Peter Muennich, Georgetown, MD (US); Luke Powers, Newark, DE (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 601 days.

(21) Appl. No.: 15/187,033

(22) Filed: Jun. 20, 2016

(65) Prior Publication Data

US 2017/0361001 A1 Dec. 21, 2017

(51) Int. Cl.
*F04D 29/22* (2006.01)
*A61M 1/10* (2006.01)
*F04D 13/02* (2006.01)
*F04D 29/42* (2006.01)
*F04D 29/62* (2006.01)
*A61M 1/36* (2006.01)

(52) U.S. Cl.
CPC ....... *F04D 29/2261* (2013.01); *A61M 1/1012* (2014.02); *A61M 1/1013* (2014.02); *A61M 1/1036* (2014.02); *A61M 1/3666* (2013.01); *F04D 13/024* (2013.01); *F04D 13/026* (2013.01); *F04D 29/2266* (2013.01); *F04D 29/426* (2013.01); *F04D 29/628* (2013.01); *A61M 2207/00* (2013.01)

(58) Field of Classification Search
USPC .......................................... 415/900
See application file for complete search history.

(56) References Cited

U.S. PATENT DOCUMENTS

| | | | | |
|---|---|---|---|---|
| 4,208,166 A * | 6/1980 | Schroeder | ............. | F04D 29/167 415/172.1 |
| 5,360,317 A * | 11/1994 | Clausen | .............. | F04D 29/0413 415/206 |
| 5,683,231 A * | 11/1997 | Nakazawa | ............ | F04D 13/026 415/900 |
| 6,155,969 A * | 12/2000 | Schima | ............... | F04D 29/0465 600/16 |
| 6,439,845 B1 * | 8/2002 | Veres | ................... | F04D 13/0666 415/206 |
| 7,431,688 B2 * | 10/2008 | Wampler | .............. | F04D 29/047 600/16 |
| 8,512,013 B2 * | 8/2013 | LaRose | ................. | A61M 1/101 417/423.12 |
| 9,011,095 B2 * | 4/2015 | Parker | ................... | F04D 29/426 415/206 |
| 9,592,326 B2 * | 3/2017 | Takatani | ............... | F04D 13/025 |
| 2006/0222533 A1 * | 10/2006 | Reeves | ................ | F04D 13/021 417/420 |

\* cited by examiner

*Primary Examiner* — Jason D Shanske
*Assistant Examiner* — Jason G Davis
(74) *Attorney, Agent, or Firm* — Fish & Richardson P.C.

(57) ABSTRACT

Extracorporeal circuit devices can be used for on-pump open-heart surgery to support surgical procedures such as coronary artery bypass grafting. In some cases, a centrifugal pump is used as part of an extracorporeal circuit. Centrifugal pump heads are described herein that induce flow on two sides of an impeller plate, and that can be conveniently mechanically assembled.

18 Claims, 13 Drawing Sheets

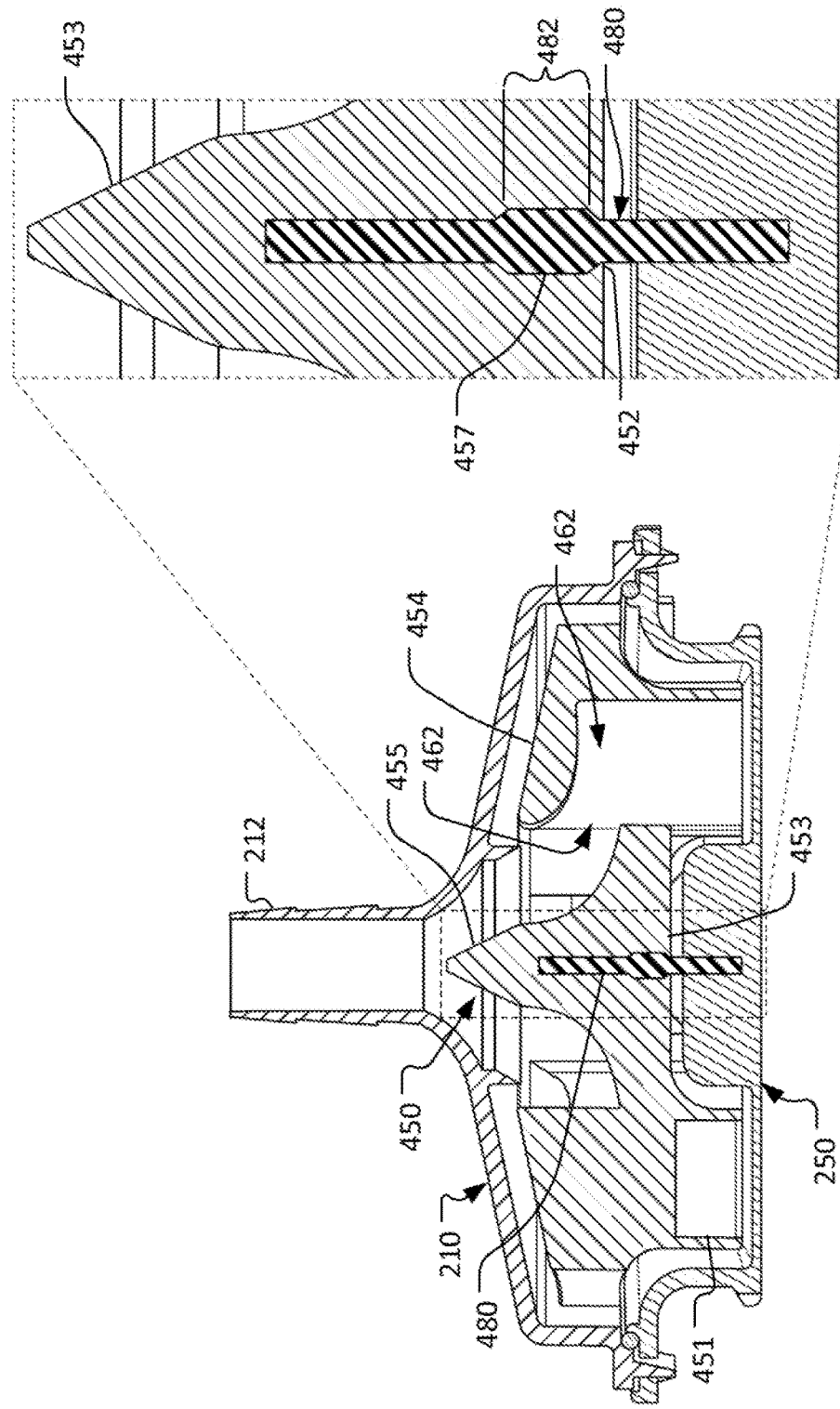

CENTRIFUGAL PUMPS FOR MEDICAL USES

BACKGROUND

1. Technical Field

This document relates to pump devices used in medical procedures. For example, this document relates to centrifugal pump devices that can be used in an extracorporeal circuit during on-pump open-heart surgery to facilitate surgical procedures such as coronary artery bypass grafting.

2. Background Information

Extracorporeal circulation is the circulation of blood outside of the body through a system that temporarily assumes an organ's functions, for example, through a heart-lung machine or artificial kidney. A centrifugal pump is sometimes utilized within an extracorporeal circuit to provide the pressurization that makes the blood flow through the circuit. For example, centrifugal pumps are sometimes used in the main line of the extracorporeal circuit in order to pump blood from a reservoir, through an oxygenator, and finally back to the patient.

In some cases, centrifugal pump heads are magnetically coupled with a drive motor. In such an arrangement, the centrifugal pump head is a passive component that is powered by the drive motor via the magnetic coupling. As a result, the drive motor can be isolated from contacting the blood, and therefore readily reused. The blood-contacting centrifugal pump head, in contrast, is a single-use disposable component.

SUMMARY

This document provides pump devices used in medical procedures. For example, this document provides centrifugal pump devices that can be used in an extracorporeal circuit during on-pump open-heart surgery to facilitate surgical procedures such as coronary artery bypass grafting. The centrifugal pump devices provided herein can also be used in other medical applications. For example, in some cases the centrifugal pump devices provided herein can be used for extracorporeal membrane oxygenation (ECMO) applications.

In one aspect, this disclosure is directed to a centrifugal pump for pumping blood in an extracorporeal circuit. The centrifugal pump includes: a housing defining an inlet port, an outlet port, and an internal space; a spindle including a first end that is fixed to the housing and a second end that is a free end; and an impeller disposed within the internal space. The impeller includes a plurality of vanes extending from a plate member and one or more magnets coupled to the plate member. The impeller defines a central hole that receives the free end of the spindle such that the impeller is freely rotatable around the spindle in relation to the housing.

Such a centrifugal pump may optionally includes one or more of the following features. The housing may include a first housing portion and a second housing portion. The first housing portion and the second housing portion may mechanically latch together to thereby form a liquid-tight seal between the first housing portion and the second housing portion. The plate member may define a plurality of slots on a side of the plate member opposite from the plurality of vanes. The plate member may define openings through the plate member between adjacent vanes of the plurality of vanes. The plate member may include two non-parallel surfaces between adjacent vanes of the plurality of vanes. The plate member may comprise a ring shape defining a central opening and an outer diameter. A diameter of the central opening may be at least ¼ of the outer diameter. The spindle may include a diametrically enlarged spindle portion having an outer diameter that is larger than other portions of the spindle. The central hole may include a diametrically enlarged hole portion having an outer diameter that is larger than other portions of the central hole. The diametrically enlarged hole portion may be configured to receive the diametrically enlarged spindle portion therein.

In another aspect, the disclosure is directed to a centrifugal pump for pumping blood in an extracorporeal circuit. The centrifugal pump includes: a housing defining an inlet port, an outlet port, and an internal space; a spindle including a first end that is fixed to the housing and a second end that is a free end; and an impeller disposed within the internal space. The impeller includes: an upper annular ring plate defining a central opening; a plurality of magnet receptacle bosses extending from the upper annular ring plate; a plurality of magnets, wherein a respective magnet is coupled to each magnet receptacle boss of the plurality of magnet receptacle bosses; and a center hub disposed between the plurality of magnet receptacle bosses. The center hub defines a central hole that receives the free end of the spindle such that the impeller is freely rotatable around the spindle in relation to the housing.

Such a centrifugal pump may optionally includes one or more of the following features. The impeller may also include a nose cone extending from the center hub. The upper annular ring plate may define a plurality of notches at an outer diameter of the upper annular ring plate. Adjacent magnet receptacle bosses of the plurality of magnet receptacle bosses may be spaced apart from each other to define slots therebetween. Openings to the slots may be defined by the adjacent magnet receptacle bosses, the upper annular ring plate, and an upper surface of the center hub. In some embodiments, the impeller does not include vanes.

In another aspect, this disclosure is directed to a method of manufacturing a centrifugal blood pump. The method includes: placing an impeller between a first pump housing portion and a second pump housing portion, the impeller comprising a plurality of vanes and one or more magnets; and latching the first pump housing portion together with the second pump housing portion, wherein the latching creates a liquid-tight seal between the first pump housing portion and the second pump housing portion.

Such a method may optionally include one or more of the following features. The first pump housing portion may include a plurality of pawls and the second pump housing portion includes a plurality of peripheral slots configured to receive the plurality of pawls. Each pawl of the plurality of pawls may include a barb on a free end of each pawl. Said latching may include pressing the first pump housing portion into engagement with the second pump housing portion. The centrifugal blood pump may include a peripheral seal that is compressed between the first pump housing portion and the second pump housing portion while the first pump housing portion is latched together with the second pump housing portion. In some embodiments, the peripheral seal is integrally-molded with the second housing portion.

Particular embodiments of the subject matter described in this document can be implemented to realize one or more of the following advantages. First, in some embodiments, the devices provided herein utilize a design that does not include ball bearings and which precludes the need for isolating bearings from blood contact. In result, a centrifugal pump head with a single internal space is facilitated. Indeed, such a design eliminates the need for sealing bearings or other internal spaces from contact with blood. Seals can be prone to failure, and can in some cases create unwelcomed noise during operation.

Second, some novel design concepts described herein can be advantageously used to tune dynamic forces asserted on an impeller of the centrifugal pump heads during operation. In result, as described further below, the impeller can be coupled within the centrifugal pump head housing in a mechanically low-complex manner. Moreover, the dynamic forces asserted on the impeller can be tuned to ensure reliable on-going magnetic coupling between the centrifugal pump head and drive motor during operation.

Third, some embodiments of the centrifugal pump heads provided herein include design features that allow the centrifugal pump heads to be produced at a lower cost than conventional designs to date. For example, material costs are reduced by the reduction of bearings and seals. In addition, the costs to assemble the centrifugal pump heads are reduced using various design features such as, but not limited to, a two-piece pump housing that mechanically latches closed to create a liquid-tight seal without the need for adhesives, welding, or hardware.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 19 is a cross-sectional view of an example centrifugal pump including the example impeller of FIG. 17.

FIG. 20 is a magnified view of a portion of FIG. 19 showing an example spindle in accordance with some embodiments.

Like reference numbers represent corresponding parts throughout.

DETAILED DESCRIPTION

This document provides pump devices used in medical procedures. For example, this document provides centrifugal pump devices that can be used in an extracorporeal circuit during on-pump open-heart surgery to facilitate surgical procedures such as, but not limited to, coronary artery bypass grafting, heart transplantation, cardiac valve implants and repairs, and the like.

Figure 1:
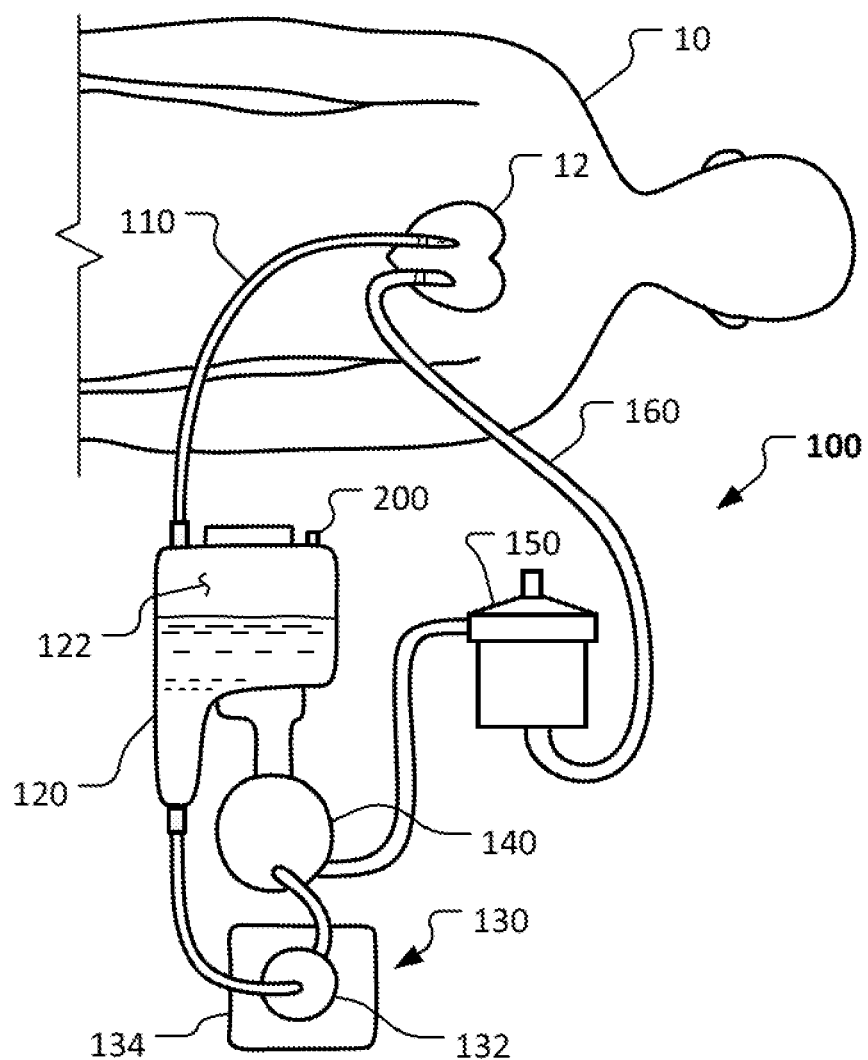
FIG. 1 is a schematic diagram of patient undergoing open-heart surgery while being supported using an extracorporeal circuit in accordance with some embodiments provided herein.

Referring to FIG. 1, a patient 10 can receive medical treatment while using an extracorporeal blood flow circuit 100 that includes a centrifugal pump system 130 as described further below. In this illustrative example, the patient 10 is undergoing a heart bypass procedure using the extracorporeal blood flow circuit 100. The circuit 100 is connected to the patient 10 at the patient's heart 12. Blood from the patient 10 is extracted from the patient 10 at the patient's heart 12; the blood is circulated through the circuit 100; and the blood is then returned to the patient's heart 12.

The extracorporeal blood flow circuit 100 includes, at least, a venous tube 110, a blood reservoir 120, the centrifugal pump system 130, an oxygenator 140, an arterial filter 150, and an arterial tube 160. The venous tube 110 is in physical contact with the heart 12 and in fluid communication with the venous side of the circulatory system of the patient 10. The venous tube 110 is also in fluid communication with an inlet to the reservoir 120.

An outlet from the reservoir 120 is connected by tubing to an inlet of a centrifugal pump head 132 of the centrifugal pump system 130. The centrifugal pump head 132 is magnetically coupled with a pump drive motor 134. The outlet of the centrifugal pump head 132 is connected by tubing to an inlet of the oxygenator 140. The outlet of the oxygenator 140 is connected by tubing to an inlet of the arterial filter 150. An outlet of the arterial filter 150 is connected to the arterial tube 160. The arterial tube 160 is in physical contact with the heart 12 and in fluid communication with the arterial side of the circulatory system of the patient 10.

Briefly, the extracorporeal blood flow circuit 100 operates by removing venous blood from the patient 10 via the venous tube 110. Blood from the venous tube 110 is deposited in the reservoir 120. At least some amount of blood is intended to be maintained in the reservoir 120 at all times during the medical procedure. Blood from the reservoir 120 is drawn from the reservoir 120 by the centrifugal pump system 130. The pressure generated by the centrifugal pump system 130 propels the blood through the oxygenator 140. In the oxygenator 140 the venous blood is enriched with oxygen. The oxygen-rich arterial blood exits the oxygenator 140, travels through the arterial filter 150, and is injected into the patient's heart 12 by the arterial tube 160.

This extracorporeal blood flow circuit 100 provides one non-limiting illustrative use of the type of the centrifugal pump head 132 to which this disclosure pertains. Other uses are also envisioned including, but not limited to, ECMO procedures.

Figure 2:
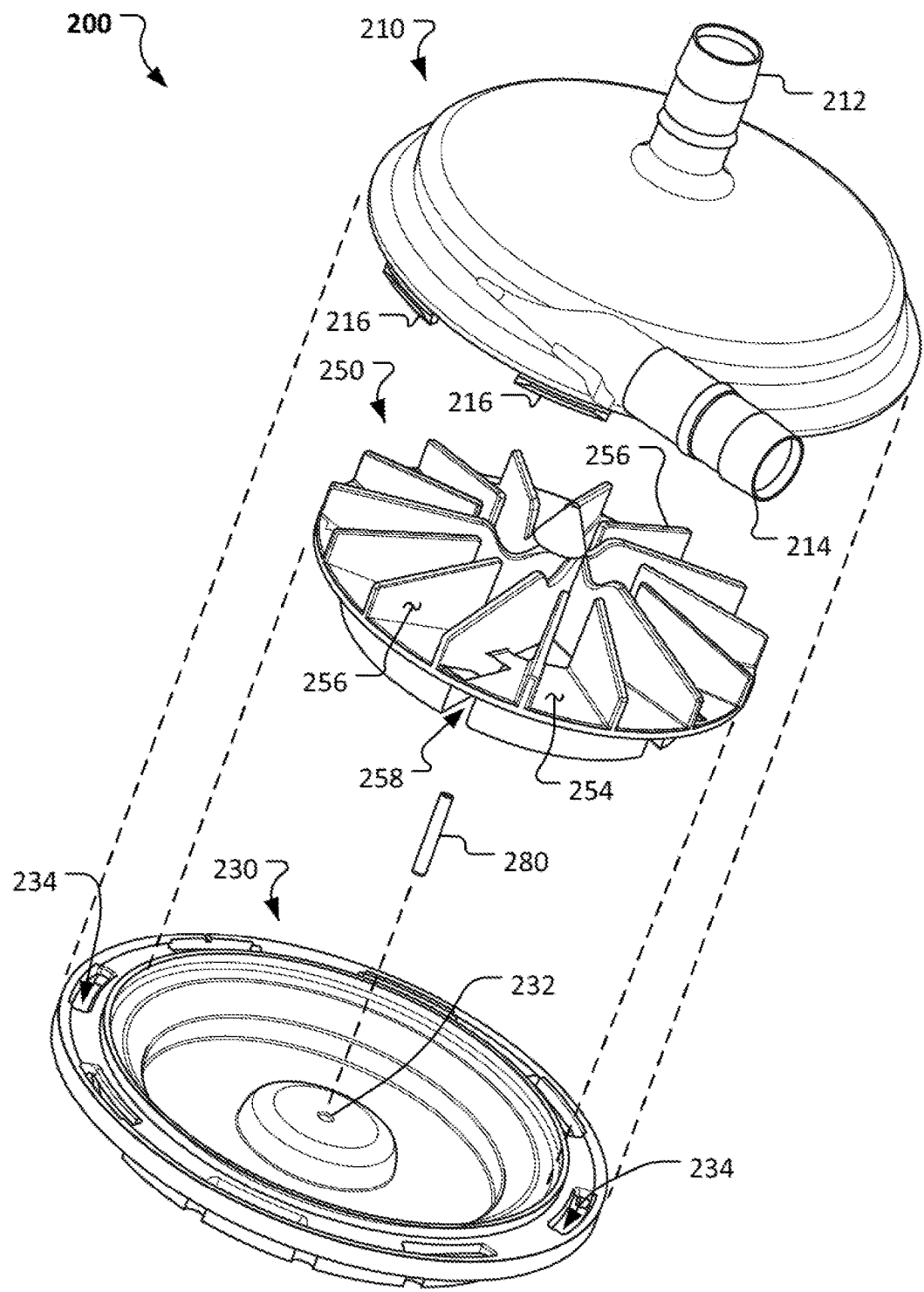
FIG. 2 is an exploded perspective view of an example centrifugal pump, in accordance with some embodiments provided herein.

Referring to FIG. 2, an example centrifugal pump head 200 is shown in an exploded perspective view. The centrifugal pump head 200 includes a first housing portion 210, a second housing portion 230, an impeller 250, and a stainless steel spindle 280.

The centrifugal pump head 200 is conveniently assembleable as follows. First, the spindle 280 is press fit into a blind hole 232 of the second housing portion 230. Alternatively, in some embodiments the spindle 280 can be insert-molded in fixed engagement with the second housing portion 230. Next, the impeller 250 is engaged with the spindle 280. A blind hole 252 (FIG. 4) slidably receives the spindle 280 using a clearance fit. Then, the first and second housing portions 210 and 230 are mechanically latched together with the impeller 250 disposed in the open space defined between the first and second housing portions 210 and 230.

The first housing portion 210 includes an inlet connector 212 defining an inlet port, an outlet connector 214 defining an outlet port, and a plurality of pawls 216. The connectors 212 and 214 are typically barbed connections as shown, but any suitable type of fluid connection can be incorporated at these inlet and outlet ports of the centrifugal pump head 200. The example centrifugal pump head 200 is a radial pump in that the inlet is in alignment with the center of the impeller 250 and the outlet is located radially outward from the impeller 250. The pawls 216 are flexible tabs with barbs that facilitate a mechanical latching mechanism between the first and second housing portions 210 and 230. That is, the plurality of pawls 216 facilitate a snap-together housing design as described further below. The example centrifugal pump head 200 is a single stage pump with a single inlet, single outlet, and a single impeller 250.

The second housing portion 230 defines the blind hole 232 and a plurality of peripheral slots 234. The blind hole 232 receives the spindle 280 in an interference fit or press fit engagement. In result, when assembled, the spindle 280 is affixed to the second housing portion 230 in a cantilevered arrangement such that the spindle 280 has a free end. The plurality of peripheral slots 234 slidably receive the plurality of pawls 216 of the first housing portion 210.

The plurality of pawls 216 and the peripheral slots 234 are designed to be complementary to each other. Each individual peripheral slot 234 of the plurality of peripheral slots 234 is configured to slidably receive and mechanically latch with an individual pawl 216 of the plurality of pawls 216.

To assemble the housing of the centrifugal pump head 200 (i.e., the housing being made of the first housing portion 210 and the second housing portion 230) the plurality of pawls 216 are aligned with the peripheral slots 234, and the housing portions 210 and 230 are pressed together until the mechanical latching is fully completed. As the housing portions 210 and 230 are pressed together, the pawls 216 will deflect radially inward in response to the process of mechanically engaging the pawls 216 with the peripheral slots 234. When the barbed ends of the pawls 216 clear the far sides of the peripheral slots 234, the pawls 216 will rebound radially outward at least to some extent. In result, the housing portions 210 and 230 will become mechanically latched together. Hence, the housing portions 210 and 230 are configured as a snap-together housing design. In other words, no gluing or welding (or other joining techniques) is needed to assemble the housing of the centrifugal pump head 200.

The impeller 250 includes a plate 254. A plurality of vanes 256 extend from the plate 254. While the impeller 250 is rotating within the housing 210/230, the vanes 256 create a pressure differential that causes fluid to flow from the inlet to the outlet of the centrifugal pump head 200. In addition, the impeller 250 defines a plurality of slots 258. The slots 258 are located on the side of the plate 254 that is opposite of the side of the plate 254 from which the vanes 256 extend. While the impeller 250 is rotating within the housing 210/230, the slots 258 create a pressure differential that causes fluid to flow from the inlet to the outlet of the centrifugal pump head 200. Hence, the pressure differentials that cause fluid to flow from the inlet to the outlet of the centrifugal pump head 200 are generated by the vanes 256 and by the slots 258.

Figure 3:
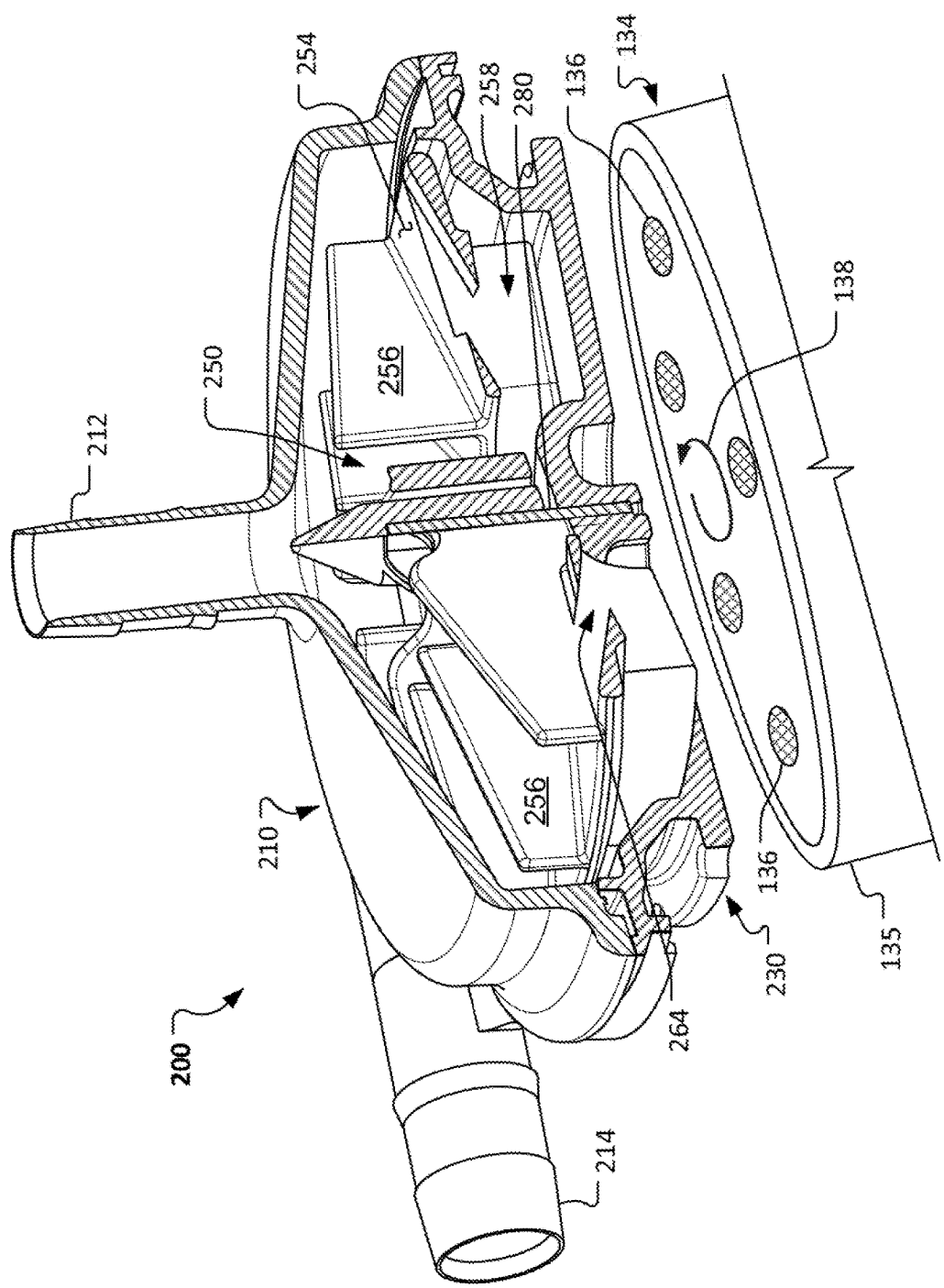
FIG. 3 is a perspective cut-away view of the example centrifugal pump depicted in FIG. 2.

Referring also to FIG. 3, the assembled centrifugal pump head 200 can be magnetically coupled with, and thereafter rotationally driven by, the pump drive motor 134. The second housing portion 230 can be configured to releasably latch with the pump drive motor 134 such that the housing 210/230 is mounted to the pump drive motor 134 in a stationary relationship to an outer casing 135 of the pump drive motor 134.

The pump drive motor 134 includes one or more magnets 136 that are magnetically attracted to one or more corresponding magnets located in or on the impeller 250. In this example, the magnets of the impeller 250 are not visible because they are encased within the impeller 250. With the magnets 136 of the pump drive motor 134 magnetically coupled with the magnets of the impeller 250, a rotation (as represented by arrow 138) of the pump drive motor 134 causes a corresponding rotation of the impeller 250 while the housing 210/230 remains stationary. In addition, the magnetic attraction between the magnets 136 of the pump drive motor 134 and the magnets of the impeller 250 supplies forces that draw the impeller 250 towards the second housing portion 230 (such that the free end of the spindle 280 contacts the bottom of the blind hole 252).

As described above, the drive motor 134 advantageously does not contact the liquid being pumped (e.g., blood). In some embodiments, other types of couplings between the drive motor and the centrifugal pump head are included. For example, a geared coupling, friction coupling, and the like can be used in some embodiments as the coupling between the drive motor and the centrifugal pump head.

In some embodiments, the assembled centrifugal pump head 200 is sterilized prior to use using a suitable sterilization technique. Such suitable sterilization techniques can include, but are not limited to, ethylene oxide (ETO) sterilization, radiation sterilization, and the like. In some embodiments, the assembled centrifugal pump head 200 is packaged in suitable packaging for maintaining a sterile condition of the centrifugal pump head 200 prior to use.

Figure 4:
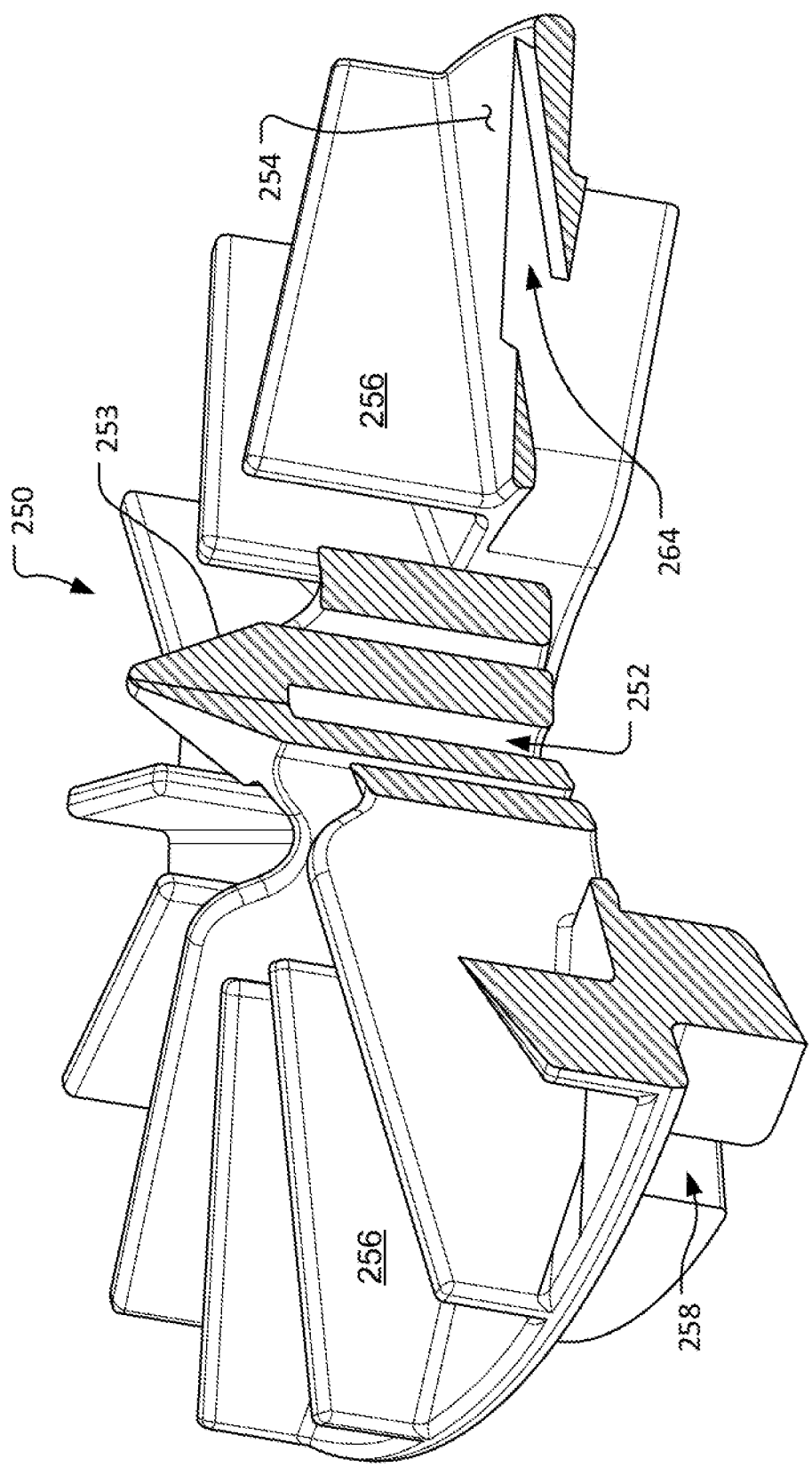
FIG. 4 is a perspective cut-away view of an example impeller of the example centrifugal pump depicted in FIG. 2.
Figure 5:
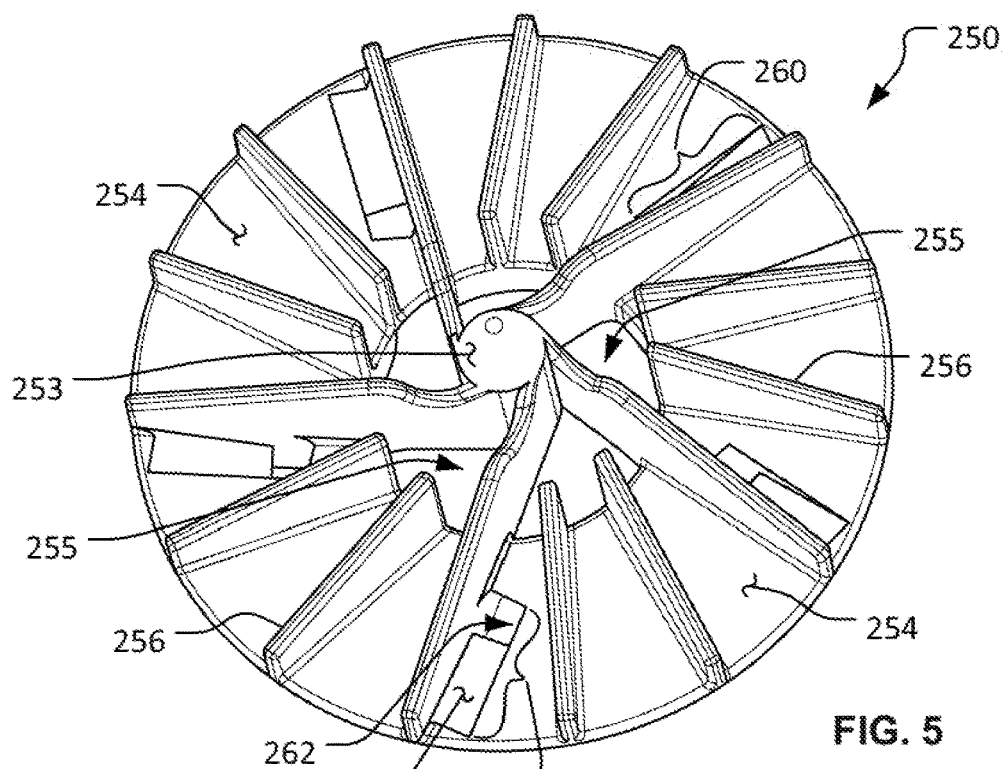
FIG. 5 is a perspective top view of the impeller of the example centrifugal pump depicted in FIG. 2.
Figure 6:
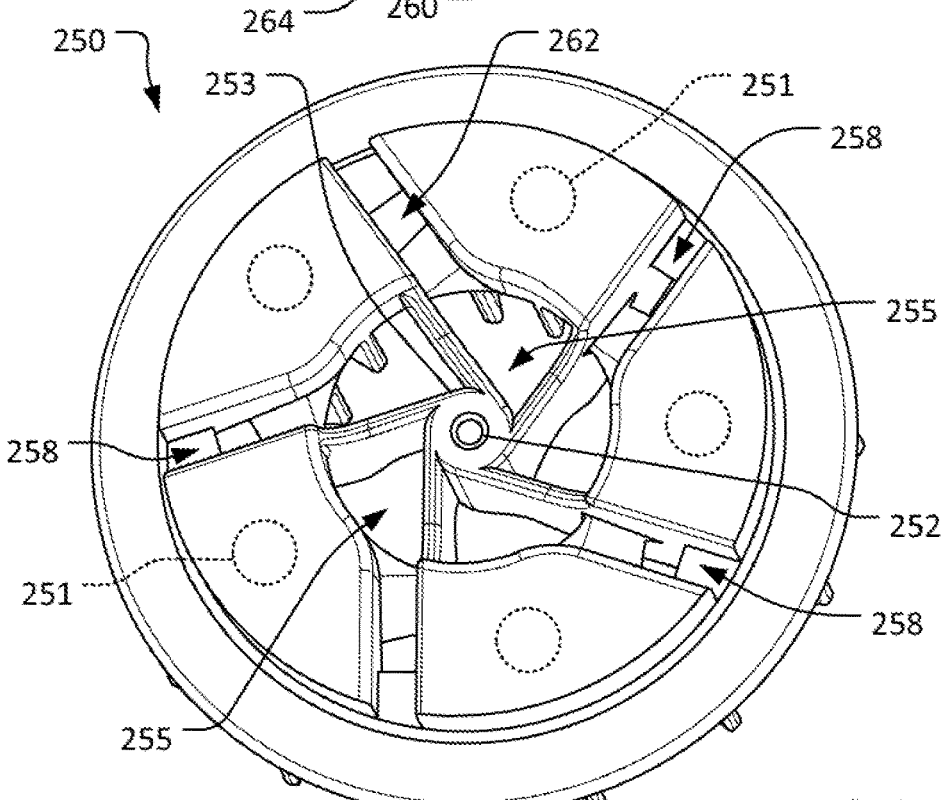
FIG. 6 is a perspective bottom view of the impeller of the example centrifugal pump depicted in FIG. 2.

Referring also to FIGS. 4-6, the example impeller 250 can generate the pressure differential to cause liquid flow through the centrifugal pump heads provided herein. The example impeller 250 includes the blind hole 252, the plate 254, the vanes 256, and the slots 258, as described above. The impeller 250 also includes a plurality of magnets 251 that can be encased within the polymeric material of the impeller 250 and a center hub 253. The vanes 256 extend from the plate 254. In the depicted embodiment, some vanes 256, but not all, are confluent with the center hub 253. The slots 258 are defined on the side of the plate 254 that is opposite of the side of the plate 254 from which the vanes 256 extend.

The blind hole 252 is designed to provide a clearance fit with the spindle 280. For example, in some embodiments a clearance of about 0.1 mm on the diameter, or about 0.08 mm on the diameter, or about 0.06 mm on the diameter, or about 0.04 mm on the diameter exists between the blind hole 252 and the spindle 280. In some embodiments, a diametrical clearance in a range of about 0.05 mm to about 0.2 mm, or about 0.05 mm to about 0.15 mm, or about 0.05 mm to about 0.10 mm, or about 0.03 mm to about 0.08 mm exists between the blind hole 252 and the spindle 280.

In some embodiments, the nominal diameter of the blind hole 252 is about 2.0 mm, or about 1.5 mm, or about 2.5 mm, or about 3.0 mm, or about 3.5 mm, or about 4.0 mm, or about 4.5 mm, or about 5.0 mm. In some embodiments, the nominal diameter of the blind hole 252 is in a range of about 1.0 mm to about 2.0 mm, or about 1.5 mm to about 2.5 mm, or about 2.0 mm to about 3.0 mm, or about 2.5 mm to about 3.5 mm, or about 3.0 mm to about 4.0 mm, or about 3.5 mm to about 4.5 mm, or about 4.0 mm to about 5.0 mm. As described further below, in some embodiments the material that makes up the walls of the blind hole 252 is selected to provide low frictional and wear resistance properties. For example, in some embodiments the material that makes up the walls of the blind hole 252 is a nylon material.

In the depicted embodiment, the plate 254 is substantially planar (i.e., the plate 254 defines a flat plane). In some embodiments, the plate 254 is inclined so as to define a conical shape. The incline can be in either direction (e.g., the plate 254 can slope either upward or downward in the direction from the peripheral edge towards the center). In some embodiments, the angle of the slope of the plate 254 is about 5 degrees, or about 10 degrees, or about 15 degrees, or about 20 degrees, or about 25 degrees, or about 30 degrees. In some embodiments, the angle of the slope of the plate 254 is in a range of about 0 degrees to about 10 degrees, or about 5 degrees to about 15 degrees, or about 10 degrees to about 20 degrees, about 15 degrees to about 25 degrees, or about 20 degrees to about 30 degrees, or about 25 degrees to about 35 degrees. In some embodiments, the plate 254 is contoured to have a slope with a curved profile.

Various design features of the vanes 256 can be selected to provide the desired performance characteristics of the impeller 250. For example, the vanes 256 can be linear or non-linear (e.g., curved or otherwise non-planar). Various numbers of vanes 256 can be included (e.g., 15 as shown, or 4, 5, 6, 7, 8, 9, 10, 11, 12, 13, 14, 16, 17, 18, 19, 20, or more than 20). The vanes 256 can extend from the plate 254 by a consistent distance, or some vanes 256 can extend from the plate 254 by greater distances than other vanes 256. The free edge of the vanes 256 (the edge opposite from the plate 254) can be parallel to the plate 254 (as shown) or askew (non-parallel) in relation to the plate 254. The vanes 256 can extend perpendicularly from the plate 254, or at an acute angle from the plate 254. In some embodiments, a second plate can be included (e.g., such that the vanes 256 are sandwiched between two plates) to provide an enclosed impeller design.

The slots 258 are defined in the impeller 250 on the opposite side of the plate 254 from which the vanes 256 extend. In the depicted embodiment, the slots 258 are defined between the magnets 251. In the depicted embodiment, 5 slots are included. In some embodiments, 2, 3, 4, 6, 7, 8, 9, 10, or more than 10 slots are included. In the depicted embodiment, the cross-sectional shapes of the slots 258 are generally rectangular. In some embodiments, the slots 258 have other cross-sectional shapes such as, but not limited to, triangular, curved, semi-circular, polygonal, and the like. In the depicted embodiment, the slots 258 are linear. In some embodiments, the slots 258 extend along paths that are curved. In the depicted embodiment, the slots 258 extend along chordal paths that are not through the center of the impeller 250. In some embodiments, the slots 258 extend along radial paths (i.e., paths extending through the center of the blind hole 232).

While the impeller 250 is rotating, both the vanes 256 and the slots 258 create pressure differentials that cause liquid flow through the centrifugal pump heads provided herein. In other words, liquid flows on each side of the plate 254. Because of Bernoulli's principle, liquid flowing over the plate 254 results in a pressure reduction on the plate 254. Since both the vanes 256 and the slots 258 generate liquid flow, pressures on each side of the plate 254 are affected in accordance with Bernoulli's principle.

The fact that pressures on each side of the plate 254 are affected because of liquid flowing over both sides of the plate 254 can be used advantageously for the centrifugal pump head designs provided herein. This is explained further as follows.

As shown in FIGS. 2 and 3, the impeller 250 rotates on the spindle 280. In the normal operational configuration, the free end of the spindle 280 is in contact with the bottom of the blind hole 252. However, the impeller 250 is not physically constrained in a particular position in the direction parallel to the longitudinal axis of the spindle 280. Rather, the impeller 250 has some freedom to move in relation to the spindle 280 (along the longitudinal axis of the spindle 280, that is). In view of the freedom of the impeller 250, the designs of the vanes 256 and the slots 258 can be selected to result in a desired resultant force on the plate 254. For example, such a desired resultant force may facilitate a reliable magnetic coupling between the impeller 250 and the motor 134, while the free end of the spindle 280 maintains contact with the end of the blind hole 252, and while avoiding excessive compressive force between the impeller 250 and the free end of the spindle 280. Such excessive compressive force could otherwise result in adverse wear and material breakdown due to excessive friction between the impeller 250 and the spindle 280.

Other design features of the impeller 250 are also included that can be selectively determined to "tune" the dynamic forces on the impeller 250. For example, the impeller 250 defines washout openings 255. The washout openings 255 are passageways through the plate 254 that allow incoming liquid to travel to the side of the plate 254 where the slots 258 are located. Increasing the size of the washout openings 255 allows more flow distribution to the slots 258 (and correspondingly less to the vanes 256).

In some embodiments, such as the depicted embodiment, the plate 254 comprises a ring shape because of the washout openings 255. The central opening of the plate's 254 ring shape (i.e., made up of the combination of all the washout openings 255) defines a central opening diameter. In some embodiments, the central opening diameter of the plate 254 is at least ¼ of the outer diameter of the plate 254. In some embodiments, the central opening diameter of the plate 254 is at least ⅓ of the outer diameter of the plate 254. In some embodiments, the central opening diameter of the plate 254 is at least ½ of the outer diameter of the plate 254.

Another design feature of the impeller 250 that can be selectively determined to tune the dynamic forces on the impeller 250 is a plurality of plate relief areas 260. The plate relief areas 260 include an opening 262 defined by the plate 254 and an inclined surface 264. The openings 262 provide passageways that can allow liquid to flow between the slots 258 and the channel spaces between adjacent vanes 256. The number of openings 262 and the size of the openings 262 can be selected to provide a desired amount of liquid transfer between the opposite sides of the plate 254.

In addition, each plate relief area 260 can include the inclined surface 264. In the case when liquid flows through the openings 262 from the slots 258 towards the channel spaces between adjacent vanes 256, force from the liquid is exerted on the inclined surfaces 264. The force exerted on the inclined surfaces 264 tends to help keep the impeller 250 seated on the spindle 280.

In the depicted embodiment, the inclined surfaces 264 are not parallel with the main surface of the plate 254. As such, the plate 254 can include two non-parallel surfaces between adjacent vanes 256 of the plurality of vanes 256. In some embodiments, the inclined surfaces 264 are at an angle of about 20 degrees in relation to the main surface of the plate 254. In some embodiments, the inclined surfaces 264 are at an angle of about 10 degrees, or about 15 degrees, or about 25 degrees, or about 30 degrees, or about 35 degrees, or about 40 degrees, or about 45 degrees in relation to the main surface of the plate 254.

While in the depicted embodiment, 5 plate relief areas 260 are included, in some embodiments 2, 3, 4, 6, 7, 8, 9, 10, or more than 10 plate relief area 260 are included. In some embodiments, no relief areas 260 are included.

Figure 16:
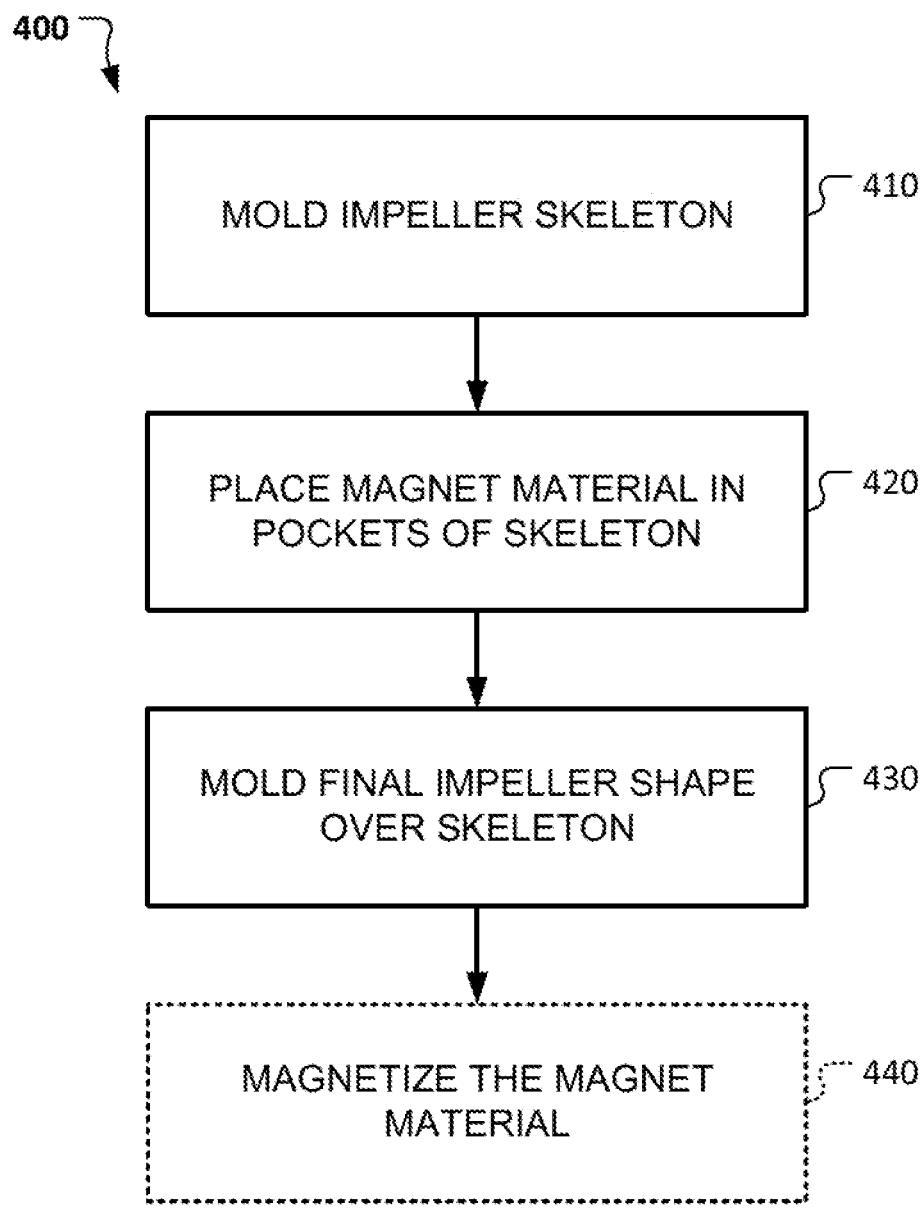
FIG. 16 is a flowchart of an example process for manufacturing a centrifugal pump impeller.

Referring also to FIG. 16, a method 400 can be performed to manufacture example impeller 250 (and the other impellers provided herein). At step 410, an impeller skeleton structure can be molded using a first thermoplastic material. The skeleton is not the entire impeller (the entire impeller shape is completed at step 430). Rather, the skeleton includes at least the walls of the blind hole 252, and pockets for the magnets 251. In some embodiments, without limitation, a nylon compound is used as the material of the impeller skeleton. For example, nylon 6-6, nylon 11, nylon 12 and other types of nylon can be used as the material of the impeller skeleton.

At step 420, magnet material is placed in the pockets of the skeleton. In some embodiments, the magnetic material is a demagnetized ceramic material, or another type of magnetize-able material. In some embodiments, the magnetic material is already magnetized (e.g., a permanent magnet such as neodymium iron boron (NdFeB), samarium cobalt (SmCo), alnico, and ceramic or ferrite magnets). In some cases, a robot or another type of automated process is used to place the magnet material in the pockets of the skeleton. In some cases, a manual process is used to place the magnet material in the pockets of the skeleton.

At step 430, a second material is molded over the skeleton containing the magnet material. This step creates the final shape of the impeller. In some embodiments, the second material can include, but is not limited to, polycarbonate, acrylonitrile butadiene styrene (ABS), acrylic, polyethylene, polyester, polypropylene, PVC, polyetheretherkeytone (PEEK), and the like.

At optional step 440, the magnet material can be magnetized. In the case where the magnet material placed in the pockets of the impeller skeleton at step 420 was not already magnetic, at step 440 the magnetic material is magnetized. Step 440 can be skipped in the case where the magnet material placed in the pockets of the impeller skeleton at step 420 was already magnetic.

Figure 7:
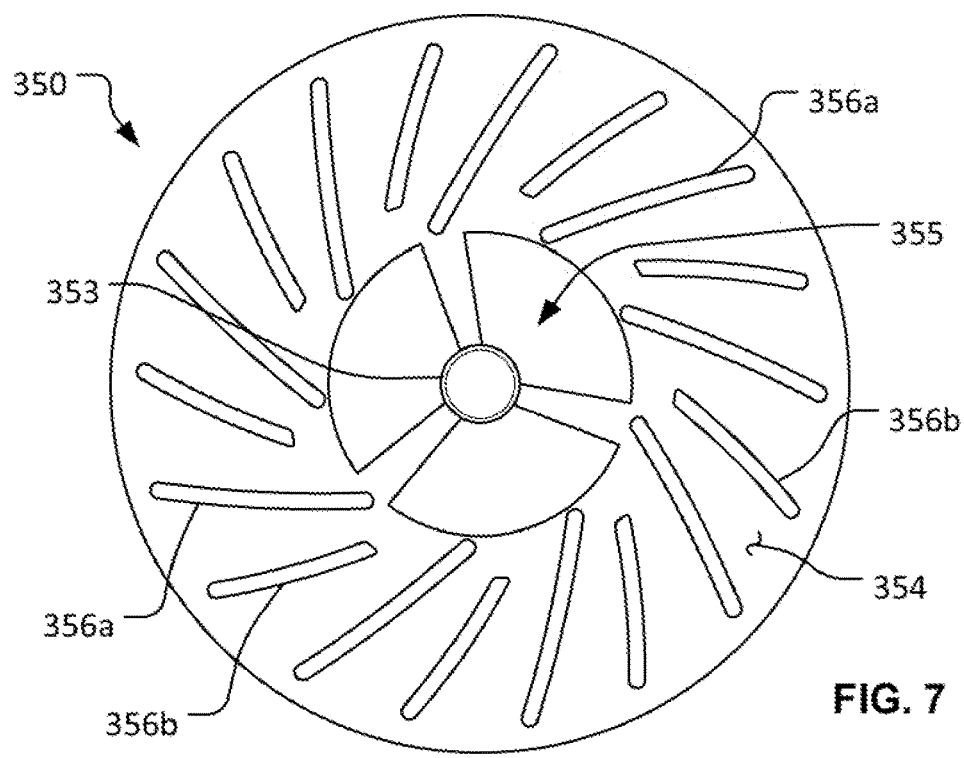
FIG. 7 is a perspective top view of another example impeller in accordance with some embodiments.
Figure 8:
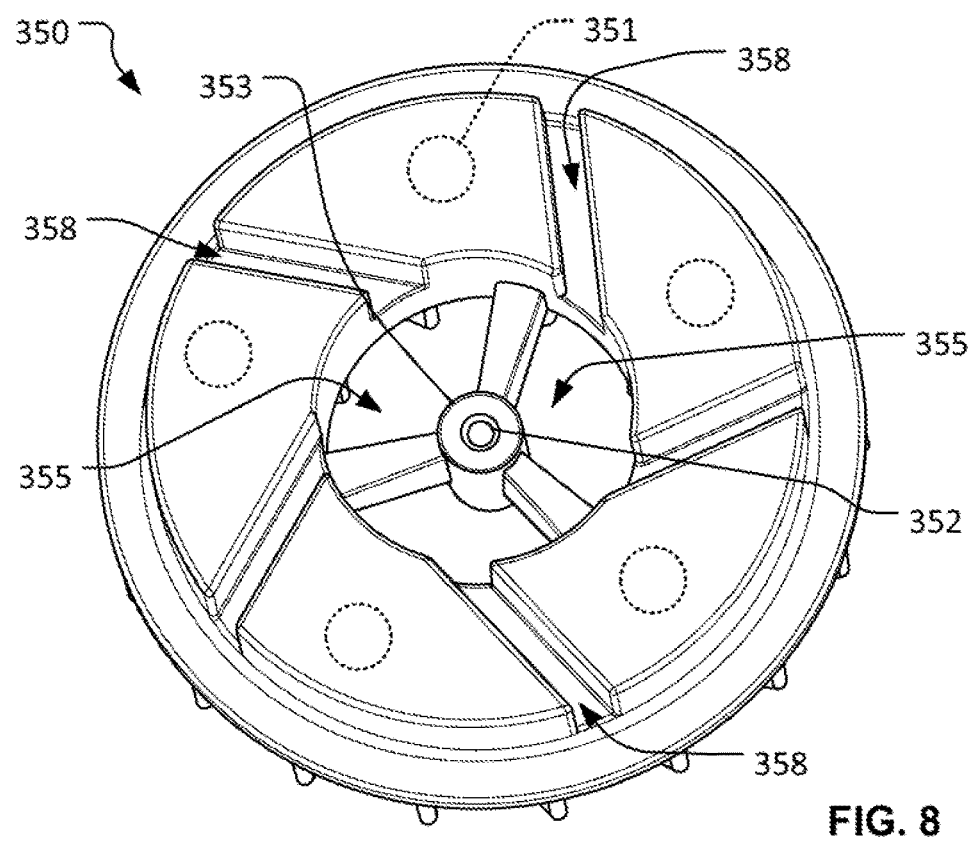
FIG. 8 is a perspective bottom view of the example impeller of FIG. 7.

Referring to FIGS. 7 and 8, another example centrifugal pump impeller 350 can generate the pressure differential to cause liquid flow through the centrifugal pump heads provided herein. The example impeller 350 includes a blind hole 352, a plate 354, washout openings 355, major vanes 356a, minor vanes 356b, slots 358, a plurality of magnets 351 and a center hub 353. The vanes 356a and 356b extend from the plate 354. The slots 358 are defined on the side of the plate 354 that is opposite of the side of the plate 354 from which the vanes 356a and 356b extend.

The example centrifugal pump impeller 350 is analogous to the example centrifugal pump impeller 250 with some exceptions. First, no plate relief areas 260 (FIGS. 5 and 6) are included in the depicted embodiment of centrifugal pump impeller 350. However, plate relief areas can be included in some embodiments of centrifugal pump impeller 350. Second, in the depicted embodiment no vanes 356a or 356b are confluent with the center hub 353. Third, in the depicted embodiment two different types of vanes 356a and 356b are included in an alternating pattern. The major vanes 356a are larger than the minor vanes 356b.

The centrifugal pump impeller 350 can be made using the materials and/or manufacturing process as described above in reference to the centrifugal pump impeller 250. Moreover, it should be understood that one or more features from one type of impeller described herein can be combined with one or more features from another type of impeller described herein. In other words, hybrid impeller designs can be created, and such hybrid designs are in the scope of this disclosure.

Figure 17:
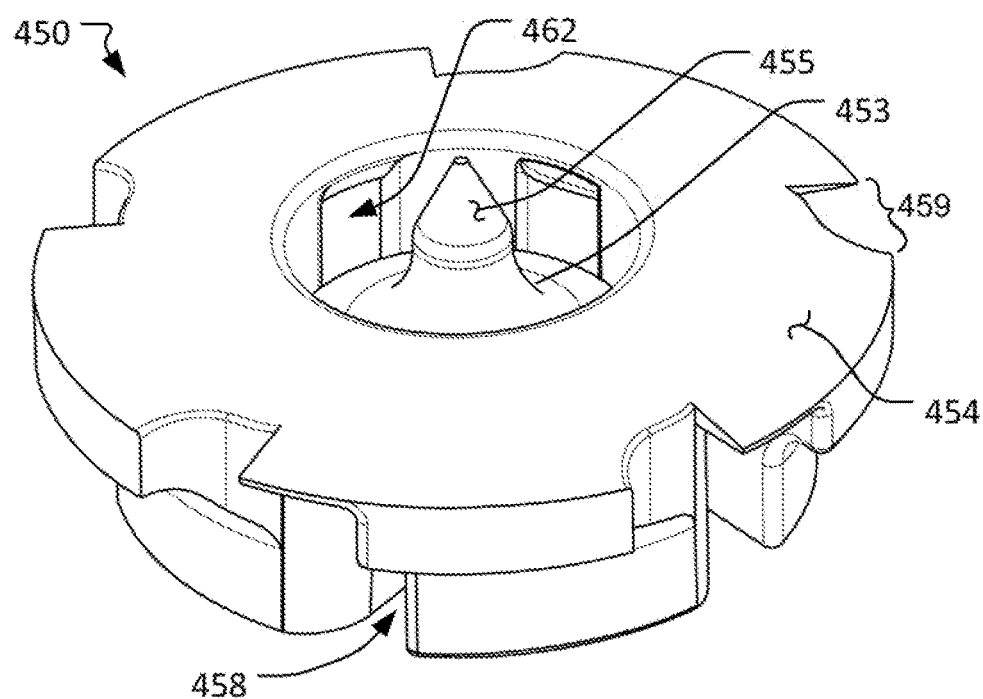
FIG. 17 is a perspective top view of another example impeller in accordance with some embodiments.
Figure 18:
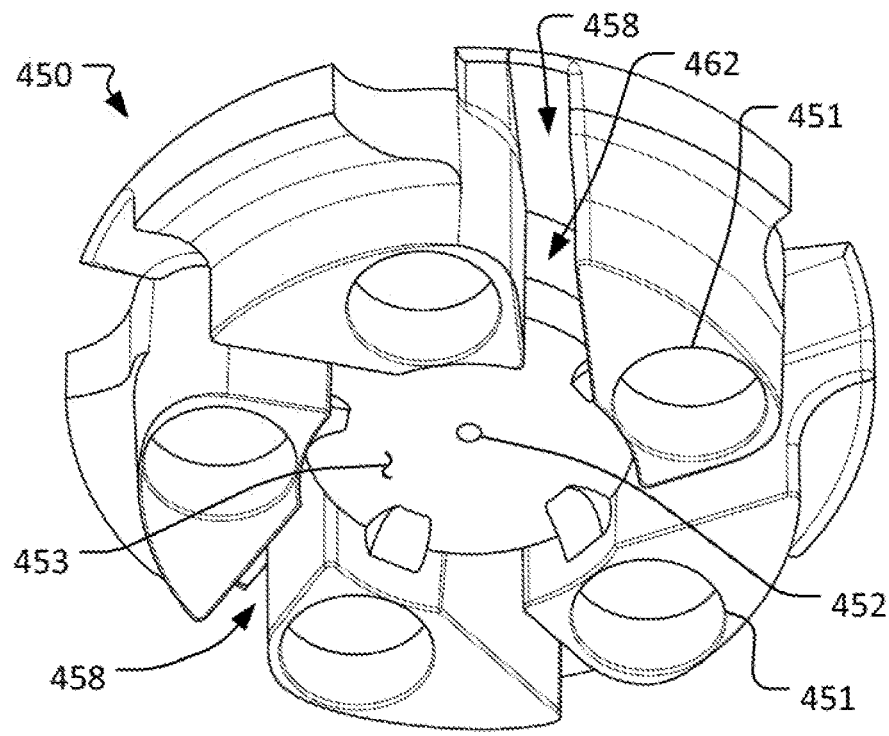
FIG. 18 is a perspective bottom view of the example impeller of FIG. 17.

Referring to FIGS. 17-19, another example centrifugal pump impeller 450 can generate the pressure differential to cause liquid flow through the centrifugal pump heads provided herein. The example impeller 450 includes a plurality of magnet receptacle bosses 451, a blind hole 452, a center hub 453, an upper annular ring plate 454, slots 458, notches 459, and openings 462.

The upper annular ring plate 454 defines a central opening (i.e., throat) below which the center hub 453 is concentrically disposed (recessed). The magnet receptacle bosses 451 extend below the upper annular ring plate 454. The center hub 453 is attached to the magnet receptacle bosses 451 such that the top surface of the center hub 453 is below the upper annular ring plate 454, except for a nose cone 455 that projects above the top surface of the upper annular ring plate 454 in the depicted embodiment. The center hub 453 defines the blind hole 452. The upper annular ring plate 454 defines the notches 459 at the outer diameter of the upper annular ring plate 454.

Adjacent magnet receptacle bosses 451 are spaced apart from each other to define the slots 458 therebetween. The slots 458 are channels through which fluids are propelled while the impeller 450 is operatively rotating.

The sides of the openings 462 are defined by adjacent magnet receptacle bosses 451. The tops of the openings 462 are defined by the upper annular ring plate 454. The bottoms of the openings 462 are defined by the upper surface of the center hub 453.

Fluid approaching the centrifugal pump impeller 450 through the inlet connector 212 of the first housing portion 210 will pass into the central opening defined by the upper annular ring plate 454, and then outward through the openings 462. The noses cone 455 and the top surface of the central hub 453 will help to gently direct the flow of the fluid towards the openings 462. After passing through the openings 462, the fluid will enter the slots 458. The fluid will be propelled outward (essentially radially) through the slots 458. Some of the fluid may pass through the notches 459. After the fluid's interactions with the impeller 450, the fluid will then exit the outlet of the first housing portion 210.

In the depicted embodiment, no vanes or slots for propelling fluid are included above the upper annular ring plate 454. Instead, all the physical features of the impeller 450 for fluid propulsion are located below the upper annular ring plate 454 (with the exception of some or all of the nose cone 455 in some embodiments).

The centrifugal pump impeller 450 can be made using the materials and/or manufacturing process as described above in reference to the centrifugal pump impeller 250. Moreover, it should be understood that one or more features from one type of impeller described herein can be combined with one or more features from another type of impeller described herein. In other words, hybrid impeller designs can be created, and such hybrid designs are in the scope of this disclosure.

Referring also to FIG. 20, in some embodiments of the centrifugal pump heads provided herein, the spindle 480 (and a corresponding blind hole 452) can be structurally configured to facilitate longitudinal restraint of the impeller 450 in relation to the spindle 480. In this context, the term "longitudinal" refers to the direction along the longitudinal axis of the spindle 480 (in the upward and downward directions as per the orientation of FIGS. 19 and 20). In other words, the spindle 480 and the blind hole 452 are configured to restrain the impeller 450 in a consistent longitudinal relationship with the spindle 480, while the impeller 450 is allowed to rotate about the spindle 480.

The spindle 480 includes a diametrically enlarged spindle portion 482. The diametrically enlarged spindle portion 482 has an outer diameter that is larger than other portions of the spindle 480. The blind hole 452 includes a diametrically enlarged bore portion 457. At the diametrically enlarged bore portion 457, the center hub 453 defines an inner diameter that is larger than other portions of the blind hole 452. A close clearance (e.g., about 0.5 mm in some embodiments, without limitation) exists between the diametrically enlarged spindle portion 482 and the diametrically enlarged bore portion 457. The clearance exists both diametrically and longitudinally. Hence, the impeller 450 can rotate freely about the spindle 480, and is free to move longitudinally a slight distance (e.g., just enough such that the rotation of the impeller 450 is not impeded).

While a physical interference exists between the outer diameter of the diametrically enlarged spindle portion 482 and the inner diameter of the blind hole 452, the center hub 453 of the impeller 450 is compliant enough to allow for a snap-together assembly technique. That is, the impeller 450 can be pushed onto the spindle 480 (or vice-versa) and the diametrically enlarged spindle portion 482 can be forced through the smaller bore of the blind hole 452 until the diametrically enlarged spindle portion 482 enters into its clearance relationship within the diametrically enlarged bore portion 457.

The diametrically enlarged bore portion 457 is complementary sized, shaped, and positioned to function simpatico with the diametrically enlarged spindle portion 482. Accordingly, if the impeller 450 tries to translate longitudinally upward in relation to the spindle 480 (e.g., in response to fluid dynamic forces), the dimensional interference between the diametrically enlarged spindle portion 482 and the diameter of the blind hole 452 will tend to longitudinally constrain the impeller 450 from moving much upward. In such a case, a bearing relationship will be created between the bottom of the diametrically enlarged spindle portion 482 and the bottom of the diametrically enlarged bore portion 457. This longitudinal constraint can advantageously help to ensure on-going robust magnetic coupling between the impeller 450 and a pump drive motor (e.g., refer to the pump drive motor 134 of FIG. 3).

Figure 9:
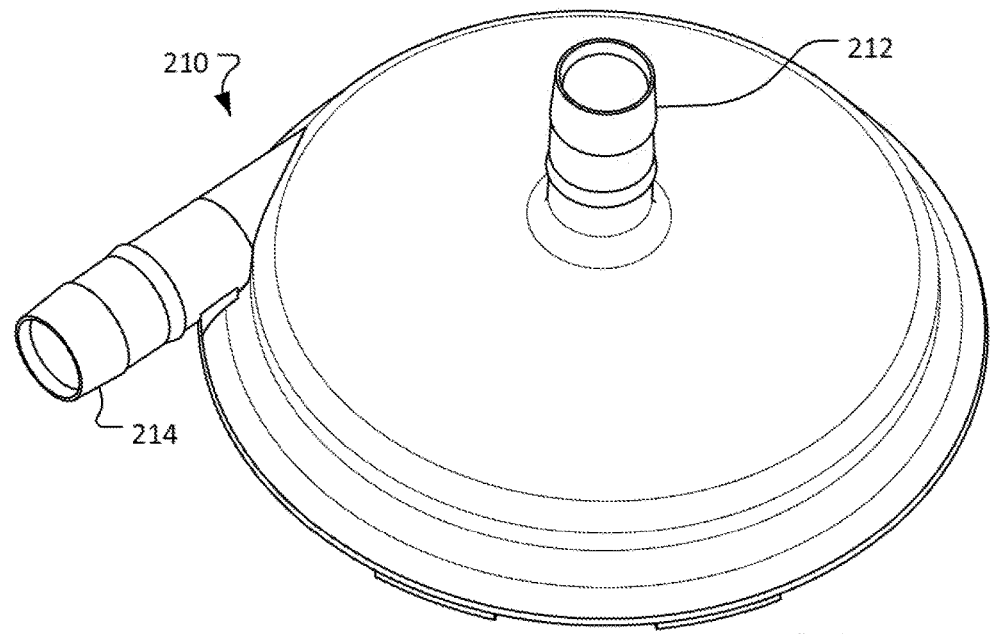
FIG. 9 is a perspective top view of a first housing portion of the example centrifugal pump depicted in FIG. 2.
Figure 10:
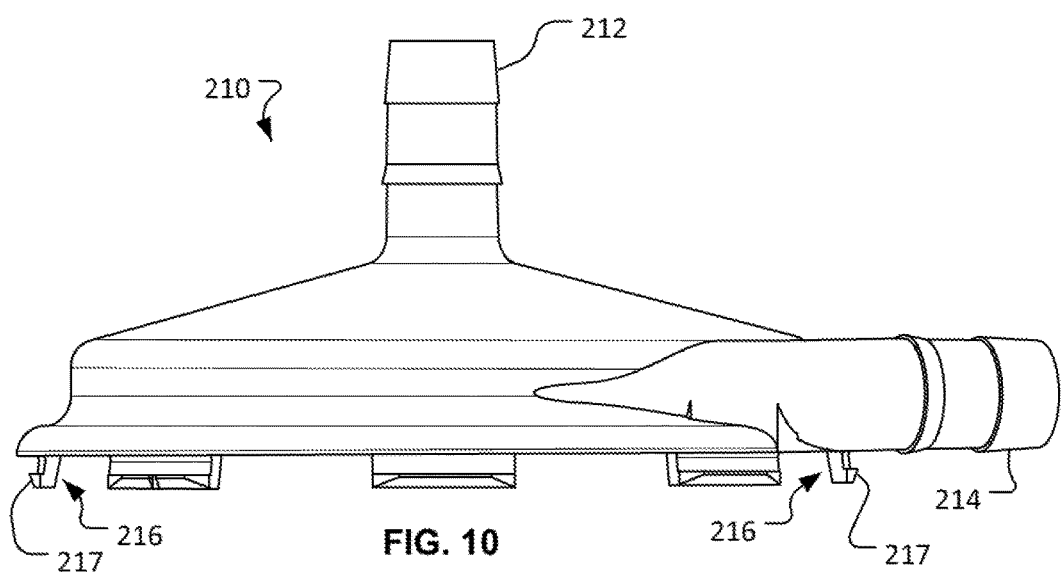
FIG. 10 is a side view of the first housing portion of the example centrifugal pump depicted in FIG. 2.
Figure 11:
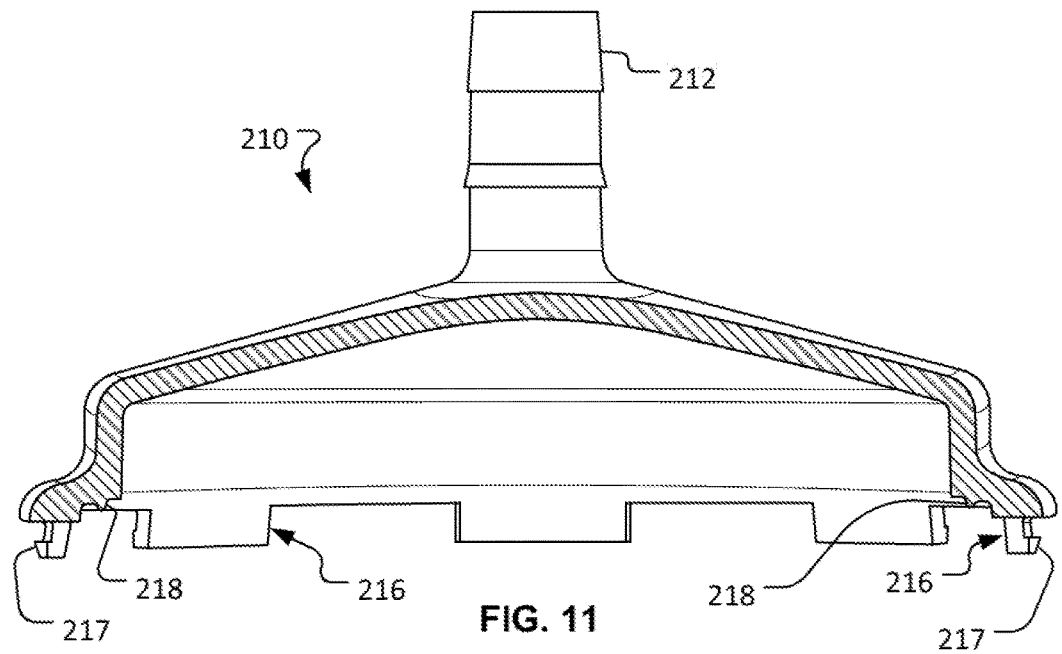
FIG. 11 is a sectional side view of the first housing portion of the example centrifugal pump depicted in FIG. 2.
Figure 12:
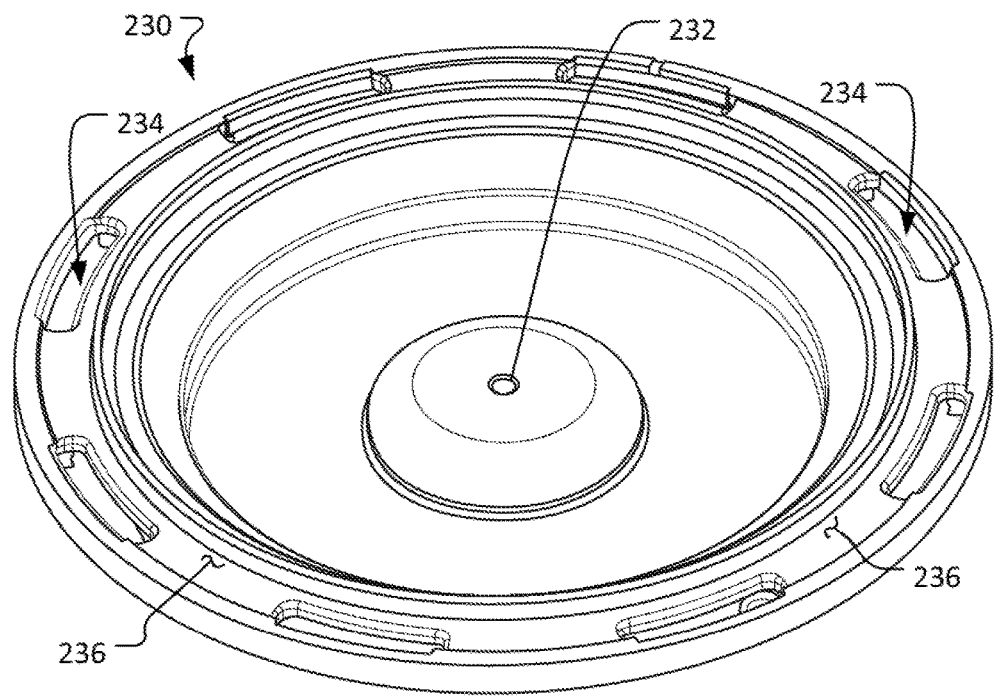
FIG. 12 is a perspective top view of a second housing portion of the example centrifugal pump depicted in FIG. 2.
Figure 13:
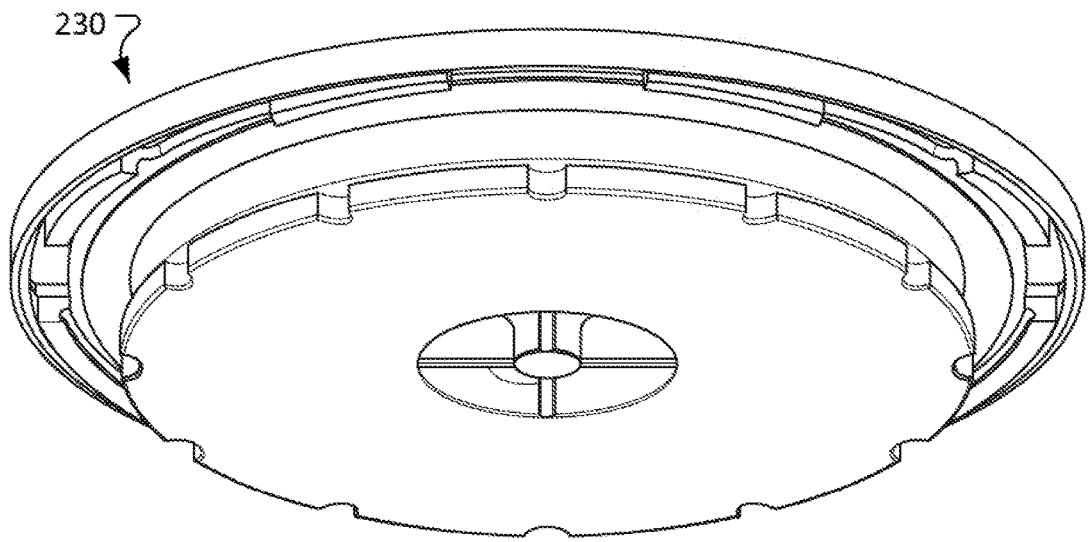
FIG. 13 is a perspective bottom view of the second housing portion of the example centrifugal pump depicted in FIG. 2.
Figure 14:
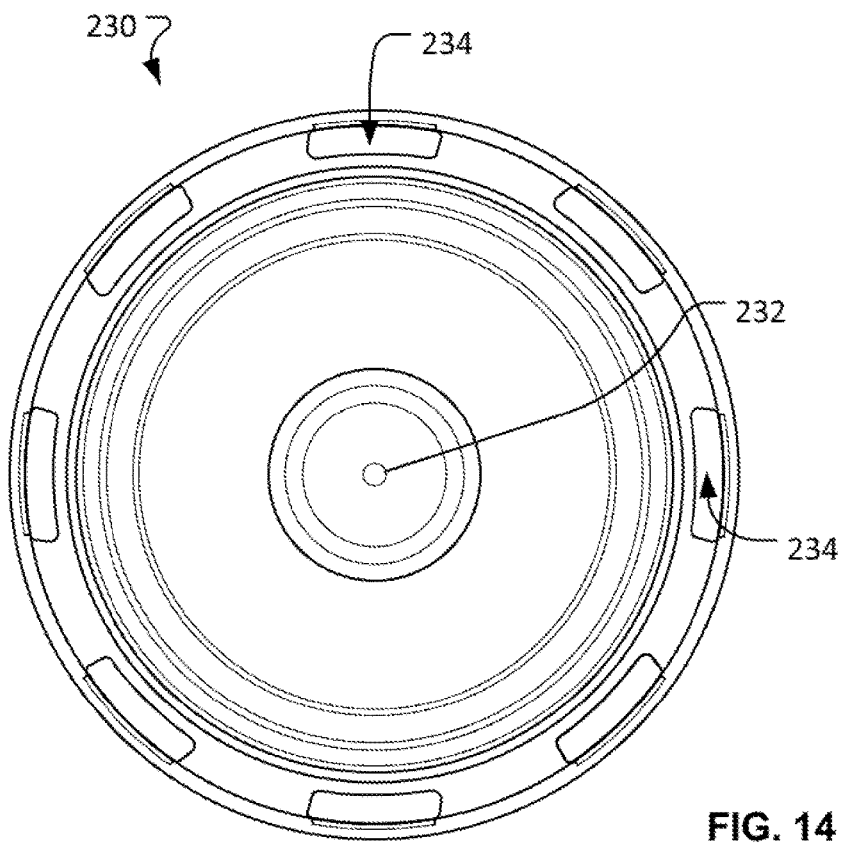
FIG. 14 is a top plan view of the second housing portion of the example centrifugal pump depicted in FIG. 2.
Figure 15:
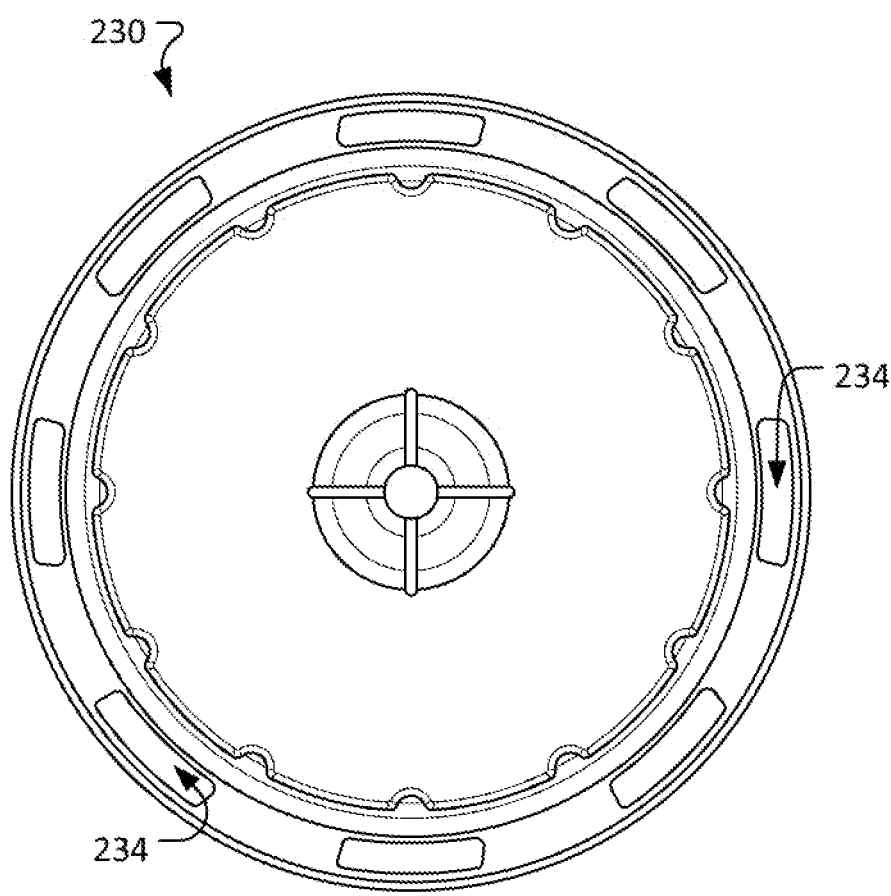
FIG. 15 is a bottom plan view of the second housing portion of the example centrifugal pump depicted in FIG. 2.

Referring to FIGS. 9-11, the first housing portion 210 is shown in greater detail. The first housing portion 210 includes the inlet connector 212, the outlet connector 214, and the plurality of pawls 216 as described above. Further, the first housing portion 210 includes barbs 217 on the free ends of the pawls 216. In addition, the first housing portion 210 includes an annular sealing ridge 218.

Referring also to FIGS. 12-15, the second housing portion 230 is shown in greater detail. The second housing portion 230 includes the blind hole 232 and the plurality of peripheral slots 234. The second housing portion 230 and includes a peripheral seal 236.

The first and second housing portions 210 and 230 can be molded from one or more types of thermoplastic material. For example, in some cases the materials of the first and second housing portions 210 and 230 can include, but are not limited to, polycarbonate, ABS, acrylic, polyethylene, polyester, polypropylene, PVC, PEEK, and the like. In some embodiments, the first and second housing portions 210 and 230 are made of the same material. In some embodiments, the first and second housing portions 210 and 230 are made from different materials.

As previously described, the first and second housing portions 210 and 230 can be snapped or latched into mechanical engagement with each other because of mating between the plurality of pawls 216 and the plurality of peripheral slots 234. Each pawl 216 includes a barb 217. As the housing portions 210 and 230 are pressed together, the pawls 216 will deflect radially inward in response to the process of mechanically engaging the pawls 216 with the peripheral slots 234. When the barbs 217 on the ends of the pawls 216 clear the far sides of the peripheral slots 234, the pawls 216 will rebound radially outward at least to some extent. In result, the housing portions 210 and 230 will become mechanically latched together.

When the housing portions 210 and 230 are latched together, a liquid-tight seal is created therebetween. That seal is enhanced by the engagement of the annular sealing ridge 218 on the first housing portion 210 with the peripheral seal 236 on the second housing portion 230. In some embodiments, the peripheral seal 236 is integrally-molded with the second housing portion 230. The peripheral seal 236 can be a moldable elastomer such as, but not limited to, fluorosilicone, silicone, VITON®, nitrile, neoprene, ethylene-propylene, polyurethane, butyl, and the like. In some embodiments, the peripheral seal 236 is a separate o-ring component that is placed between the housing portions 210 and 230 prior to latching them together. When the housing portions 210 and 230 are latched together, the annular sealing ridge 218 can indent the peripheral seal 236 to create a robust liquid-tight seal.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A centrifugal pump for pumping blood in an extracorporeal circuit, the centrifugal pump comprising:
    a housing defining an inlet port, an outlet port, and an internal space;
    a spindle including a first end that is fixed to the housing and a second end that is a free end; and
    an impeller disposed within the internal space, the impeller comprising a plurality of vanes extending from a plate member and one or more magnets coupled to the plate member,
    wherein the impeller defines a central hole that receives the free end of the spindle such that the impeller is freely rotatable around the spindle in relation to the housing, and
    wherein, between adjacent vanes of the plurality of vanes and on the same side of the plate member as the plurality of vanes, the plate member includes a main surface and an inclined surface that is non-parallel to the main surface.

2. The centrifugal pump of claim 1, the housing comprising a first housing portion and a second housing portion, wherein the first housing portion and the second housing portion mechanically latch together to thereby form a liquid-tight seal between the first housing portion and the second housing portion.

3. The centrifugal pump of claim 1, wherein the plate member defines a plurality of slots on a side of the plate member opposite from the plurality of vanes.

4. The centrifugal pump of claim 1, wherein the plate member defines openings through the plate member between adjacent vanes of the plurality of vanes.

5. The centrifugal pump of claim 1, wherein the plate member comprises a ring shape defining a central opening and an outer diameter, wherein a diameter of the central opening is (i) at least ¼ of the outer diameter and (ii) less than the outer diameter.

6. The centrifugal pump of claim 1, wherein the spindle includes a diametrically enlarged spindle portion having an outer diameter that is larger than other portions of the spindle.

7. The centrifugal pump of claim 6, wherein the central hole includes a diametrically enlarged hole portion having an outer diameter that is larger than other portions of the central hole, and wherein the diametrically enlarged hole portion is configured to receive the diametrically enlarged spindle portion therein.

8. The centrifugal pump of claim 1, wherein an angle between the main surface and the inclined surface is 10 degrees.

9. The centrifugal pump of claim 1, wherein an angle between the main surface and the inclined surface is 15 degrees.

10. The centrifugal pump of claim 1, wherein an angle between the main surface and the inclined surface is 20 degrees.

11. The centrifugal pump of claim 1, wherein an angle between the main surface and the inclined surface is 25 degrees.

12. The centrifugal pump of claim 1, wherein an angle between the main surface and the inclined surface is 30 degrees.

13. The centrifugal pump of claim 1, wherein an angle between the main surface and the inclined surface is 35 degrees.

14. The centrifugal pump of claim 1, wherein an angle between the main surface and the inclined surface is 40 degrees.

15. The centrifugal pump of claim 1, wherein an angle between the main surface and the inclined surface is 45 degrees.

16. A centrifugal pump for pumping blood in an extracorporeal circuit, the centrifugal pump comprising:
    a housing defining an inlet port, an outlet port, and an internal space;
    a spindle including a first end that is fixed to the housing and a second end that is a free end; and
    an impeller disposed within the internal space, the impeller comprising:
        an upper annular ring plate defining a central opening and a plurality of notches at an outer diameter of the upper annular ring plate;
        a plurality of magnet receptacle bosses extending from the upper annular ring plate, wherein adjacent magnet receptacle bosses of the plurality of magnet receptacle bosses are spaced apart from each other to define a plurality of slots, and wherein a respective notch of the plurality of notches is located between each pair of adjacent slots of the plurality of slots;

a plurality of magnets, wherein a respective magnet is coupled to each magnet receptacle boss of the plurality of magnet receptacle bosses;

a center hub disposed between the plurality of magnet receptacle bosses, the center hub defining a central hole that receives the free end of the spindle such that the impeller is freely rotatable around the spindle in relation to the housing; and openings to the slots, the openings to the slots fully peripherally enclosed by: (i) the adjacent magnet receptacle bosses, (ii) the upper annular ring plate, and (iii) an upper surface of the center hub.

17. The centrifugal pump of claim 16, wherein the impeller further comprises a nose cone extending from the center hub.

18. The centrifugal pump of claim 16, wherein the impeller does not include vanes.

\* \* \* \* \*